United States Patent
Andrews (10) Patent No.: US 9,867,565 B2
(45) Date of Patent: Jan. 16, 2018

(54) SIDELINE TEST TO DETECT CONCUSSIONS THAT AFFECT VISUAL, PROPRIOCEPTIVE, OR VESTIBULAR BRAIN FUNCTIONS

(71) Applicant: Craig Andrews, Loudon, TN (US)

(72) Inventor: Craig Andrews, Loudon, TN (US)

(*) Notice: Subject to any disclaimer, the term of this patent is extended or adjusted under 35 U.S.C. 154(b) by 125 days.

(21) Appl. No.: 14/791,396

(22) Filed: Jul. 3, 2015

(65) Prior Publication Data

US 2017/0000403 A1    Jan. 5, 2017

(51) Int. Cl.
*A61B 5/00* (2006.01)
*A61B 5/16* (2006.01)

(52) U.S. Cl.
CPC .......... *A61B 5/4064* (2013.01); *A61B 5/162* (2013.01); *A61B 5/165* (2013.01); *A61B 5/4005* (2013.01); *A61B 5/4094* (2013.01); *A61B 5/7435* (2013.01); *A61B 2562/0219* (2013.01)

(58) Field of Classification Search
CPC .......... A61B 2562/0219; A61B 5/4005; A61B 5/4064; A61B 5/4094; A61B 5/4076; A61B 5/16; A61B 5/165; A61B 5/162; A61B 5/168; A61B 5/7435; A61B 5/744; A61B 5/7445; A61B 3/0091; A61B 3/02; A61B 3/024; A61B 3/028; A61B 3/032
See application file for complete search history.

(56) References Cited

U.S. PATENT DOCUMENTS

| | | |
|---|---|---|
| 9,064,370 B1 | 6/2015 | Daniel |
| 2007/0027406 A1 | 2/2007 | LaPlaca et al. |
| 2011/0205167 A1* | 8/2011 | Massengill ............ A61B 3/113 345/173 |
| 2014/0024971 A1* | 1/2014 | Bunn ....................... A61B 5/11 600/595 |

OTHER PUBLICATIONS

Straus, "Balance Error Scoring System: Useful Tool in Assessing Concussion", MomsTeam, Aug. 18, 2014. Retrieved from <http://momsteam.com/health-safety/BESS-balance-error-scoring-system-assessing-balance-in-concussion> on Apr. 4, 2017.*

(Continued)

*Primary Examiner* — David J McCrosky
(74) *Attorney, Agent, or Firm* — CroseLaw LLC; Bradley D. Crose (57) ABSTRACT

A method for testing a subject to detect a reduction in cerebral function presumably resulting from mild traumatic brain injury, that affects visual, proprioceptive, and vestibular brain functions includes: providing a user interface, input device, and portable computer into the hands of the test subject suspected of having mild traumatic brain injury; providing an icon on the user interface visible to the subject; rotating the subject holding the computer a predetermined number of revolutions, at a predetermined rate of rotation, to engage the vestibular system of the subject prior to testing; aligning, by the subject, the icon on the screen of the user interface in alignment with a test administrator; maintaining the alignment of the icon on the screen and the test administrator throughout the rotations; and conducting a real-time (Continued)

test for mild traumatic brain injury utilizing the user interface, the user input device, and the associated computer.

21 Claims, 4 Drawing Sheets

(56) References Cited

OTHER PUBLICATIONS

Straus, "King-Devick Test: An Important Part of Sideline Concussion Screening Battery", MomsTeam, Jun. 11, 2013. Retrieved from <http://momsteam.com/king-devick-test-important-part-sideline-concussion-screening> on Apr. 4, 2017.*
Berg Balance Scale retrieved from <http://www.aahf.info/pdf/Berg_Balance_Scale.pdf> on Mar. 31, 2017.*
K-D (King Devick) test, Impact test, found online, http://www.google.com/url?sa=t&rct=j&q=&esrc=s&source=web&cd=1&ved=0CCUQFjAA&url=http%3A%2F%2Fmedicine.utah.edu%2Fpmr%2Fconference%2Fpresentations%2F2013%2FAnne%2520Mucha%25202013.pdf&ei=vsDkVPreGPPIsQT2uoCADw&usg=AFQjCNHpZiQ1UGbA09rYSo80bllZp-A7Aw&sig2=eXIUfLnOfL-OW4pxpq_1WA&bvm=bv.85970519,d.cWc, Jun. 27, 2015.
U.S. Appl. No. 13/074,980, Portable System and Method for Detecting Neurological Issue, filed Mar. 9, 2011, not published, but accessed online Jun. 27, 2015 through Public PAIR.

* cited by examiner

SIDELINE TEST TO DETECT CONCUSSIONS THAT AFFECT VISUAL, PROPRIOCEPTIVE, OR VESTIBULAR BRAIN FUNCTIONS

FIELD OF THE INVENTION

The technology described herein relates generally to methods, systems, and devices for the testing of subjects in real-time for the possible occurrence of a brain concussion or traumatic brain injury. More specifically, this technology relates to a sideline test to detect concussions that affect visual, proprioceptive, or vestibular brain functions. Furthermore, this technology relates to a testing and assessment device on which the sideline test to detect concussions that affect visual, proprioceptive, or vestibular brain functions operates for interactivity with the subject.

BACKGROUND OF THE INVENTION

A concussion is a mild traumatic brain injury that is generally defined as a head injury with a temporary loss of brain function. Mild traumatic brain injury, such as a concussion, can occur, for example, with sports injuries, bicycle accidents, car accidents, falls, blows to the head, and so forth.

A concussion can create various physical, cognitive, somatic, and emotional systems. By way of example, a concussed person may experience a headache, feeling in a fog, being emotionally distraught, amnesia, slow reaction times, and sleep irregularities. Some symptoms may be so subtle that they are not recognized.

Risk for concussions is particularly high for certain athletic competitions such as football, rugby, and soccer. Should mild traumatic brain injury occur during such an event, speedy assessment of the subject is critical. If the assessment shows positively that the subject is concussed, the subject clearly should not return to the game and should be provided the immediate and proper medical care needed.

Known tests and methods for assessment of subjects who may have received a concussion are inadequate. Others have attempted to overcome these deficiencies with new tests and methods for assessment; however, these tests and methods have been found also to have various shortcomings.

Related utility patents known in the art include the following:

U.S. Pat. No. 9,064,370, issued to Daniel on Jun. 23, 2015, discloses a method for conducting a sports technology reality show that includes a concussion tracker device on the sidelines.

Related patent application publications known in the art include the following:

U.S. Patent Application Publication No. 2007/0027406, filed by LaPlaca et al. and published on Feb. 1, 2007, discloses a display enhanced testing for concussions and mild traumatic brain injuries.

U.S. Patent Application Publication No. 2011/0205167, filed by Massengill and published on Aug. 25, 2011, discloses a brain concussion screening method and apparatus.

Related pending patent applications known in the art, yet not published, include the following:

Ser. No. 13/074,980, Portable System and Method for Detecting Neurological Issue, filed Mar. 9, 2011 by Daniel, not published, but accessed online 2015-06-27 through Public PAIR.

Related non-patent literature known in the art includes the following:

The K-D (King Devick) test and Impact test, VISUAL & VESTIBULAR ABNORMALITIES FOLLOWING CONCUSSION.

The foregoing patent and other information reflect the state of the art of which the inventor is aware and are tendered with a view toward discharging the inventor's acknowledged duty of candor in disclosing information that may be pertinent to the patentability of the technology described herein. It is respectfully stipulated, however, that the foregoing patent and other information do not teach or render obvious, singly or when considered in combination, the inventor's claimed invention.

BRIEF SUMMARY OF THE INVENTION

In various exemplary embodiments, the technology described herein provides a sideline test to detect concussions that affect visual, proprioceptive, or vestibular brain functions. Furthermore, this technology relates to a testing and assessment device on which the sideline test to detect concussions that affect visual, proprioceptive, or vestibular brain functions operates for interactivity with the subject.

In one exemplary embodiment, the technology described herein provides a method for testing a subject to detect a reduction in cerebral function presumably resulting from a mild traumatic brain injury, such as a concussion, that affects one or more of visual, proprioceptive, and vestibular brain functions. The method includes: providing a user interface, a user input device, and an associated portable hand-held computer into the hands of the test subject suspected of having a mild traumatic brain injury, such as a concussion; providing an icon on the screen of the user interface visible to the test subject; rotating the test subject holding the portable hand-held computer a predetermined number of revolutions, and at a predetermined rate of rotation, to engage the vestibular system of the test subject prior to testing for mild traumatic brain injury or concussion; aligning, by the test subject, the icon on the screen of the user interface in alignment with a test administrator; and maintaining the alignment of the icon on the screen of the user interface and the test administrator throughout the rotations.

In at least one embodiment, the method also includes: conducting a real-time test for mild traumatic brain injury or concussion utilizing the user interface, the user input device, and the associated portable hand-held computer; displaying at least one test icon on the user interface for interaction and response from the test subject; detecting user interaction and response by the test subject on the user interface; analyzing with the computer the user interaction, response, and input of the test subject; and determining with the computer whether the input test subject exhibits a reduction in cerebral function presumably resulting from a mild traumatic brain injury, such as a concussion.

In at least one embodiment, the method further includes comparing a real-time performance and results of the test subject with a previously established baseline performance.

In at least one embodiment, the method also includes: conducting a real-time saccades test for mild traumatic brain injury or concussion utilizing the user interface, the user input device, and the associated portable hand-held computer; displaying repeatedly a white dot on a black screen on the user interface for interaction and response from the test subject; detecting user interaction and response by the test subject on the user interface, wherein the test subject is attempting to touch the white dot for a predetermined number of attempts; recording a plurality of data points to measure a distance between the white dot and a location on the user interface touched by the test subject trying to touch the white dot; analyzing with the computer the user interaction, response, and input of the test subject; and determining with the computer whether the input test subject exhibits a reduction in cerebral function presumably resulting from a mild traumatic brain injury, such as a concussion.

In at least one embodiment, the method further includes: conducting a real-time saccades test for mild traumatic brain injury or concussion utilizing the user interface, the user input device, and the associated portable hand-held computer; displaying repeatedly a white dot on a black screen on the user interface for interaction and response from the test subject, and wherein each white dot further comprises an alphabetical letter within the dot; detecting user interaction and response by the test subject on the user interface, wherein the test subject is attempting to provide an input based on a cognitive decision about the letter displayed in the white dot and its relation to a predetermined test criteria provided to the test subject; recording a plurality of data points to measure and record the input data from the test subject; analyzing with the computer the user interaction, response, and input of the test subject; and determining with the computer whether the input test subject exhibits a reduction in cerebral function presumably resulting from a mild traumatic brain injury, such as a concussion.

In at least one embodiment, the method also includes: conducting a real-time pursuits test for mild traumatic brain injury or concussion utilizing the user interface, the user input device, and the associated portable hand-held computer; displaying a moving icon on the user interface for interaction and response from the test subject; detecting user interaction and response by the test subject on the user interface, wherein the test subject is attempting to touch and follow by fingertip the moving icon for a predetermined number of attempts; recording a plurality of data points to measure the accuracy of the test subject in following the moving icon; analyzing with the computer the user interaction, response, and input of the test subject; and determining with the computer whether the input test subject exhibits a reduction in cerebral function presumably resulting from a mild traumatic brain injury, such as a concussion.

In at least one embodiment, the an alternative pursuits method also includes: conducting a real-time pursuits test for mild traumatic brain injury or concussion utilizing the user interface, the user input device, and the associated portable hand-held computer; displaying a moving icon on the user interface for interaction and response from the test subject, wherein the moving icon further is displaying within the icon a changing number or letter that changes at a predetermined time interval; detecting user interaction and response by the test subject on the user interface, wherein the test subject is attempting to follow the moving icon with his or her eyes and responding on the user interface based upon a direction in which the changing number or letter changes or where it falls in sequence, for a predetermined number of attempts; recording a plurality of data points to measure the accuracy of the test subject in following the moving icon; analyzing with the computer the user interaction, response, and input of the test subject; and determining with the computer whether the input test subject exhibits a reduction in cerebral function presumably resulting from a mild traumatic brain injury, such as a concussion.

In at least one embodiment, the method also includes: conducting a real-time combined fixation, vestibular, and proprioception test for mild traumatic brain injury or concussion utilizing the user interface, the user input device, and the associated portable hand-held computer; displaying a moving icon on the user interface that visually represents a ball bearing that can roll around freely on the screen for interaction and response from the test subject; displaying a circular shape on the user interface, wherein the object of the test subject is to keep the moving icon within the circular shape and not roll out; detecting user interaction and response by the test subject on the user interface, wherein the test subject is attempting to keep the moving icon within the circular shape and not roll out for a predetermined number of attempts; recording a plurality of data points to measure the accuracy of the test subject in following the moving icon; analyzing with the computer the user interaction, response, and input of the test subject; and determining with the computer whether the input test subject exhibits a reduction in cerebral function presumably resulting from a mild traumatic brain injury, such as a concussion.

In at least one embodiment, the method further includes: conducting a real-time photo differentiation recognition test for mild traumatic brain injury or concussion utilizing the user interface, the user input device, and the associated portable hand-held computer; displaying a photo on the user interface depicting a typical object or person but having at least one atypical attribute to the object or person; displaying subsequently, and in varying degrees of rotation, a plurality of photos with only one of the plurality matching the one with at least one atypical attribute, such that the test subject must select a photo pair that matches; detecting user interaction and response by the test subject on the user interface, wherein the test subject is attempting to match a pair of photos having at least one atypical attribute to the object or person; recording a plurality of data points to measure the accuracy of the test subject in matching a pair of photos having at least one atypical attribute to the object or person; analyzing with the computer the user interaction, response, and input of the test subject; and determining with the computer whether the input test subject exhibits a reduction in cerebral function presumably resulting from a mild traumatic brain injury, such as a concussion.

In at least one embodiment, the method also includes: selecting and conducting two or more the following tests on the test subject in order: conducting a real-time saccades test for mild traumatic brain injury or concussion utilizing the user interface, the user input device, and the associated portable hand-held computer; conducting a real-time pursuits test for mild traumatic brain injury or concussion utilizing the user interface, the user input device, and the associated portable hand-held computer; conducting a real-time combined fixation, vestibular, and proprioception test for mild traumatic brain injury or concussion utilizing the user interface, the user input device, and the associated portable hand-held computer; and conducting a real-time photo differentiation recognition test for mild traumatic brain injury or concussion utilizing the user interface, the user input device, and the associated portable hand-held computer.

In at least one embodiment, the method further includes: rotating, before and/or between any one or more the real-time saccades test, real-time pursuits test, the real-time combined fixation, vestibular, and proprioception test, and the real-time photo differentiation recognition test, the test subject holding the portable hand-held computer a predetermined number of revolutions, and at a predetermined rate of rotation, to engage the vestibular system of the test subject prior to testing for mild traumatic brain injury or concussion.

In at least one embodiment, the method also includes: using a computer program on the computer to time the speed of turning a the test subject prior to conducting a test when rotating the test subject holding the portable hand-held computer a predetermined number of revolutions, and at a predetermined rate of rotation, to engage the vestibular system of the test subject prior to testing for mild traumatic brain injury or concussion.

In at least one embodiment, the method further includes using a rotating image held by the test subject while rotating in order to adjust the speed of rotation.

In at least one embodiment, the method also includes using a cumulative sum of a plurality of distances measured each portion of a second from a moving circle on the computer user interface to determine how well the test subject maintains visual contact with a target.

In at least one embodiment, the method also includes wherein the computer device utilized further comprises a plurality of accelerometers in the computer device to determine reaction abilities of the test subject.

In at least one embodiment, the method further includes wherein the computer device utilized further comprises a plurality of accelerometers in the computer device to monitor changes over time in a reaction ability of the test subject.

In at least one embodiment, the method also includes recording a reaction of the test subject to a force being applied without their being aware of the timing or the amount of force.

In at least one embodiment, the method further includes using unknown forces to determine reaction time changes over time in the test subject.

In at least one embodiment, the method also includes using alphabetical order of letters in the test conducted to determine cognitive damage caused by concussion or mild traumatic brain injury.

In another exemplary embodiment, the technology described herein provides a computer program product for testing a subject to detect a reduction in cerebral function presumably resulting from a mild traumatic brain injury, such as a concussion, that affects one or more of visual, proprioceptive, and vestibular brain functions. The computer program product includes: a computer readable storage medium readable by a processor of a computer and configured to store instructions for execution by the processor for performing a method including: providing a user interface, a user input device, and an associated portable hand-held computer into the hands of the test subject suspected of having a mild traumatic brain injury, such as a concussion; providing an icon on the screen of the user interface visible to the test subject; rotating the test subject holding the portable hand-held computer a predetermined number of revolutions, and at a predetermined rate of rotation, to engage the vestibular system of the test subject prior to testing for mild traumatic brain injury or concussion; aligning, by the test subject, the icon on the screen of the user interface in alignment with a test administrator; maintaining the alignment of the icon on the screen of the user interface and the test administrator throughout the rotations; conducting a real-time test for mild traumatic brain injury or concussion utilizing the user interface, the user input device, and the associated portable hand-held computer; displaying at least one test icon on the user interface for interaction and response from the test subject; detecting user interaction and response by the test subject on the user interface; analyzing with the computer the user interaction, response, and input of the test subject; and determining with the computer whether the input test subject exhibits a reduction in cerebral function presumably resulting from a mild traumatic brain injury, such as a concussion.

In another exemplary embodiment, the technology described herein provides an apparatus for testing a subject to detect a reduction in cerebral function presumably resulting from a mild traumatic brain injury, such as a concussion, that affects one or more of visual, proprioceptive, and vestibular brain functions. The apparatus including: a user interface; a user input device; and an associated portable hand-held computer configured for placement into the hands of the test subject suspected of having a mild traumatic brain injury, such as a concussion; the computer being programmed to: provide an icon on the screen of the user interface visible to the test subject; rotate the test subject holding the portable hand-held computer a predetermined number of revolutions, and at a predetermined rate of rotation, to engage the vestibular system of the test subject prior to testing for mild traumatic brain injury or concussion; align, by the test subject, the icon on the screen of the user interface in alignment with a test administrator; maintain the alignment of the icon on the screen of the user interface and the test administrator throughout the rotations; conduct a real-time test for mild traumatic brain injury or concussion utilizing the user interface, the user input device, and the associated portable hand-held computer; display at least one test icon on the user interface for interaction and response from the test subject; detect user interaction and response by the test subject on the user interface; analyze with the computer the user interaction, response, and input of the test subject; and determine with the computer whether the input test subject exhibits a reduction in cerebral function presumably resulting from a mild traumatic brain injury, such as a concussion.

Thus, advantageously, the technology described herein provides a sideline test and testing and assessment device to detect concussions that affect visual, proprioceptive, or vestibular brain functions. Known systems do not involve the vestibular or the proprioceptive systems which are at risk in concussions. A majority of concussed individuals become dizzy or nauseated from their vestibular system. Known tests do not address this problem. The technology described herein provides many advantages and features over the known systems.

There has thus been outlined, rather broadly, the more important features of the technology in order that the detailed description thereof that follows may be better understood, and in order that the present contribution to the art may be better appreciated. There are additional features of the technology that will be described hereinafter and which will form the subject matter of the claims appended hereto. In this respect, before explaining at least one embodiment of the technology in detail, it is to be understood that the invention is not limited in its application to the details of construction and to the arrangements of the components set forth in the following description or illustrated in the drawings. The technology described herein is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the technology described herein.

Further objects and advantages of the technology described herein will be apparent from the following detailed description of a presently preferred embodiment which is illustrated schematically in the accompanying drawings.

BRIEF DESCRIPTION OF THE DRAWINGS

The technology described herein is illustrated with reference to the various drawings, in which like reference numbers denote like device components and/or method steps, respectively, and in which.

DETAILED DESCRIPTION OF THE INVENTION

Before describing the disclosed embodiments of this technology in detail, it is to be understood that the technology is not limited in its application to the details of the particular arrangement shown here since the technology described is capable of other embodiments. Also, the terminology used herein is for the purpose of description and not of limitation.

In various exemplary embodiments, the technology described herein provides a sideline test to detect concussions that affect visual, proprioceptive, or vestibular brain functions. Furthermore, this technology relates to a testing and assessment device on which the sideline test to detect concussions that affect visual, proprioceptive, or vestibular brain functions operates for interactivity with the subject.

Figure 1:
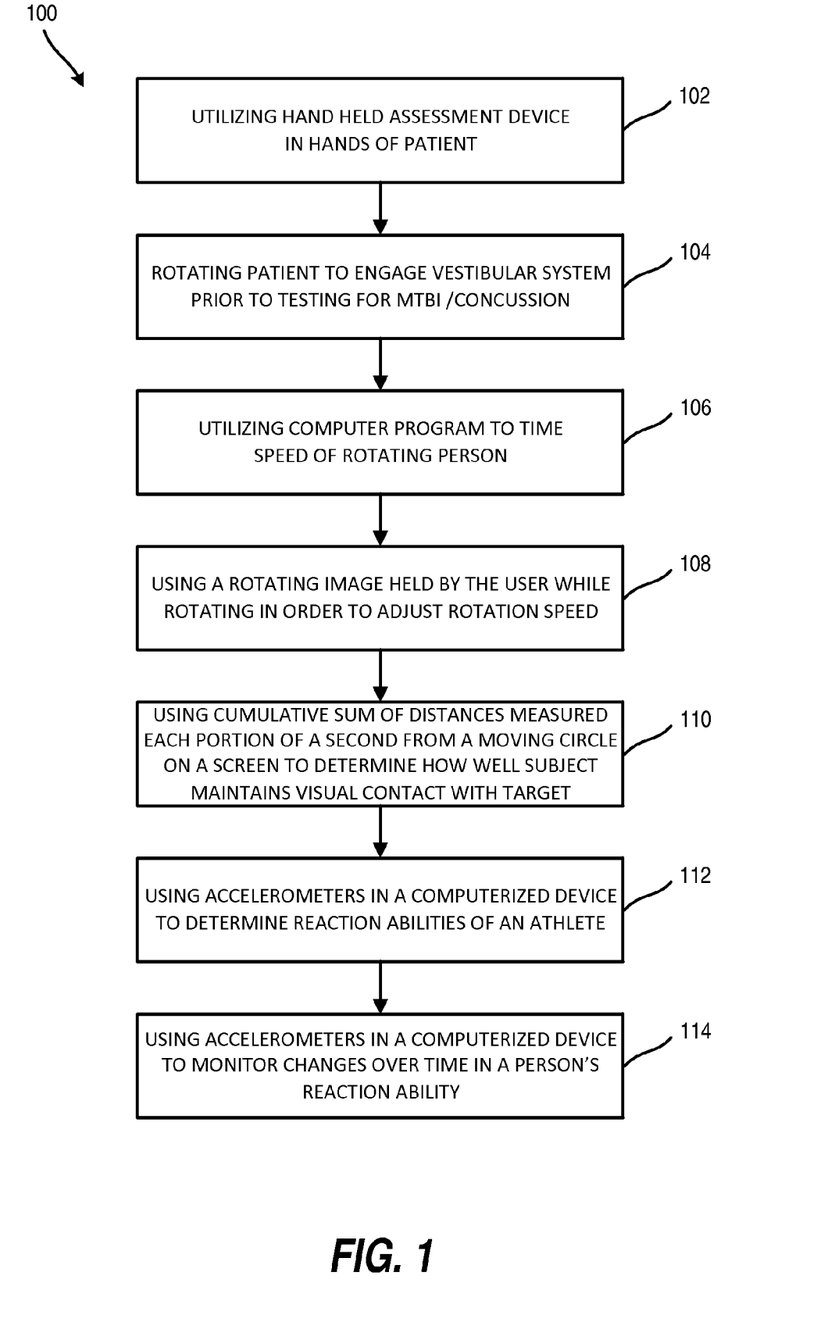
FIG. 1 is a flowchart diagram depicting a method and various method steps for testing a subject to detect a reduction in cerebral function presumably resulting from a mild traumatic brain injury, such as a concussion, that affects one or more of visual, proprioceptive, and vestibular brain functions, according to an embodiment of the technology described herein.
Figure 3:
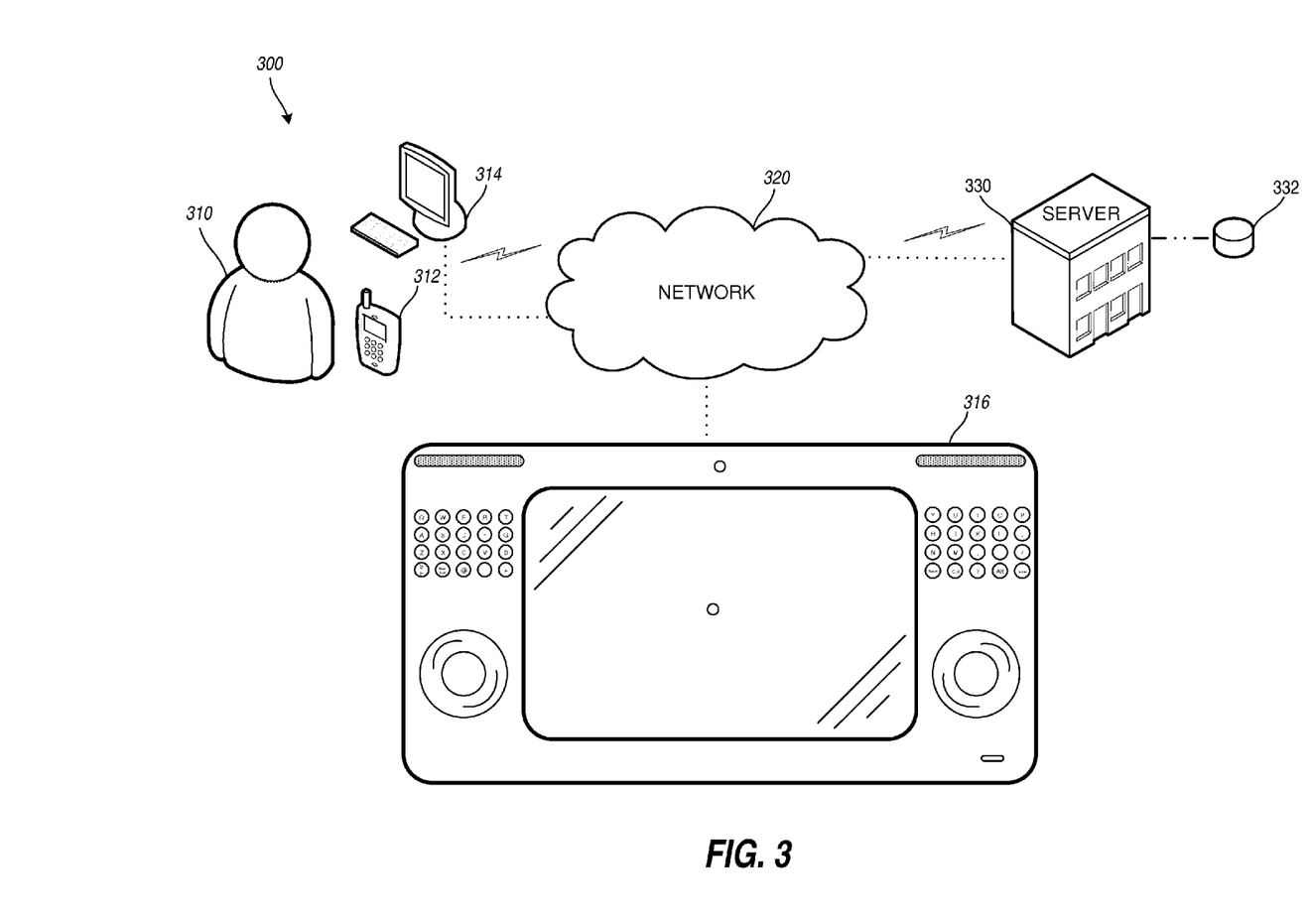
FIG. 3 is a schematic diagram depicting a system testing a subject to detect a reduction in cerebral function presumably resulting from a mild traumatic brain injury, such as a concussion, that affects one or more of visual, proprioceptive, and vestibular brain functions, according to an embodiment of the technology described herein.

In one exemplary embodiment, the technology described herein provides a method for testing a subject 310 to detect a reduction in cerebral function presumably resulting from a mild traumatic brain injury, such as a concussion, that affects one or more of visual, proprioceptive, and vestibular brain functions. The method includes providing 102 a user interface 316, a user input device (screen of 316), and an associated portable hand-held computer 312, 314, and/or 316 into the hands of the test subject 310 suspected of having a mild traumatic brain injury, such as a concussion. The method includes providing an icon 108 on the screen of the user interface 316 visible to the test subject 310. The method includes rotating 104 the test subject 310 holding the portable hand-held computer 316 a predetermined number of revolutions, and at a predetermined rate of rotation, to engage the vestibular system of the test subject 310 prior to testing for mild traumatic brain injury or concussion. The method includes aligning, by the test subject 310, the icon on the screen of the user interface 316 in alignment with a test administrator. The method includes maintaining the alignment of the icon on the screen of the user interface 316 and the test administrator throughout the rotations.

By way of example, and not of limitation, the rotation process includes the following in at least one embodiment. In order to bring in the vestibular system, rotate the patient test subject three times at a rate of one rotation each 5 seconds. The way that we do this is have the patient hold a portable computer tablet with their non-dominant hand under the tablet and steady it with their dominant hand. An arrow will appear on the screen. The patient is to rotate their body while holding the tablet such that they should keep the arrow pointing at the person giving the test at all times. So it will require that the person (with the aid of the examiner) rotates counter-clockwise three times.

In at least one embodiment, the method also includes conducting a real-time test for mild traumatic brain injury or concussion utilizing the user interface, the user input device, and the associated portable hand-held computer. The method includes displaying at least one test icon on the user interface 316 for interaction and response from the test subject 310. The method includes detecting user interaction and response by the test subject on the user interface 110, for example. The method includes analyzing with the computer the user interaction, response, and input of the test subject. The method includes determining with the computer whether the input test subject exhibits a reduction in cerebral function presumably resulting from a mild traumatic brain injury, such as a concussion.

In at least one embodiment, the method further includes comparing a real-time performance and results of the test subject 310 with a previously established baseline performance.

The test scenario, by way of example, may include four minutes of testing using the user computer device. Normals (controls) are tested as well as those with recent concussions and those of concussions that are not recent. From this data, for example, it can be determined if it is required to use the test in a pretest situation (true comparison) or if the concussed prove to be so outside the normal range, then the test may be accurate enough without pretesting.

Figure 2:
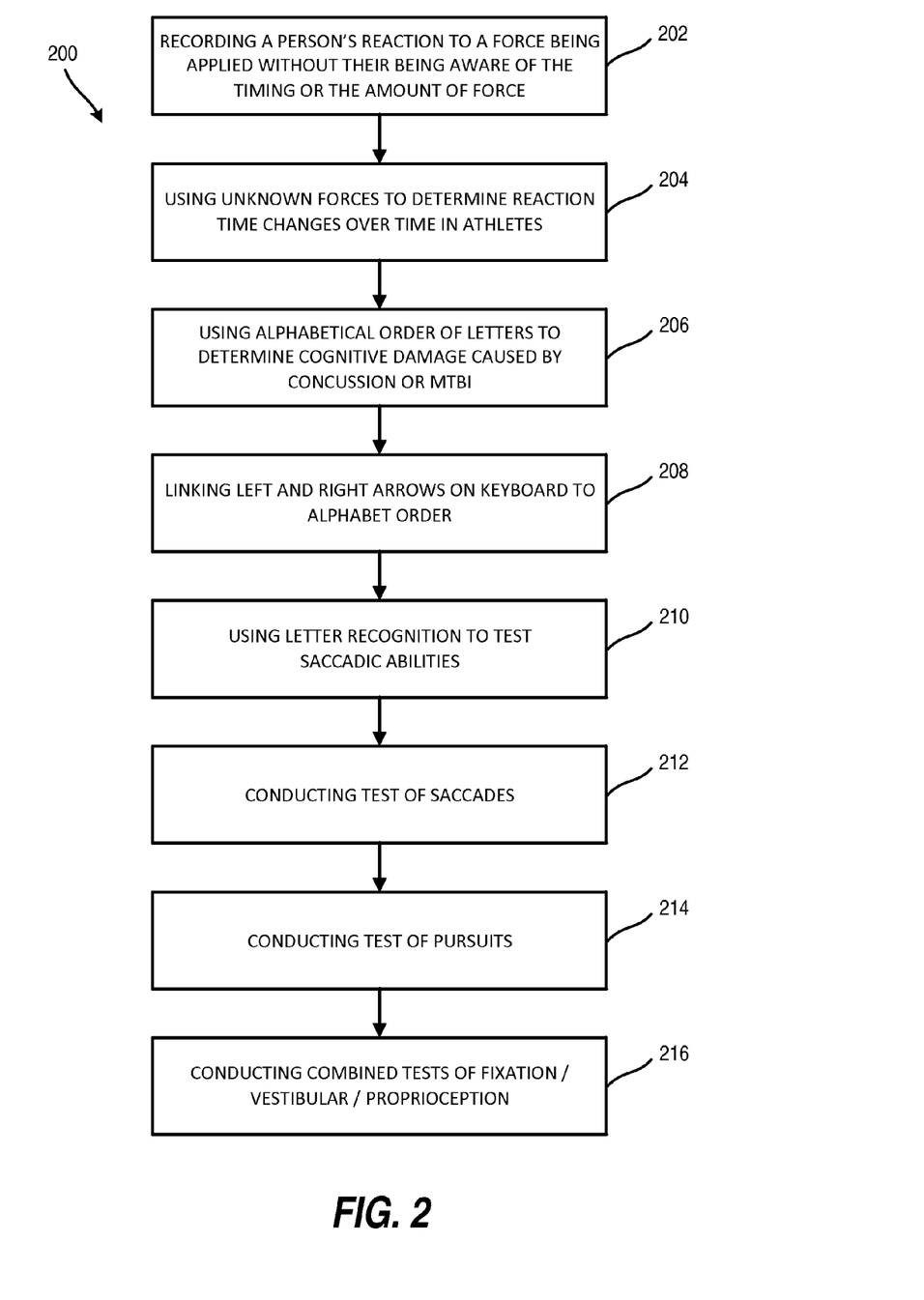
FIG. 2 is a flowchart diagram depicting a method and various method steps for testing a subject to detect a reduction in cerebral function presumably resulting from a mild traumatic brain injury, such as a concussion, that affects one or more of visual, proprioceptive, and vestibular brain functions, according to an embodiment of the technology described herein.

In at least one embodiment, the method also includes conducting a real-time saccades test 212 for mild traumatic brain injury or concussion utilizing the user interface, the user input device, and the associated portable hand-held computer. The method includes displaying repeatedly a white dot on a black screen on the user interface 316 for interaction and response from the test subject. The method includes detecting user interaction and response by the test subject 310 on the user interface 316, wherein the test subject is attempting to touch the white dot for a predetermined number of attempts. The method includes recording a plurality of data points 110 to measure a distance between the white dot and a location on the user interface 316 touched by the test subject 310 trying to touch the white dot. The method includes analyzing with the computer 316 the user interaction, response, and input of the test subject 310. The method includes determining with the computer whether the input test subject exhibits a reduction in cerebral function presumably resulting from a mild traumatic brain injury, such as a concussion.

By way of example, and not of limitation, in this test the patient touches where they see the white dot on a black screen. They will be tested for accuracy on 20 dots, for example. The data will keep track of distance from the actual spot.

Also by way of example, and not of limitation, in this test certain parts of the brain are involved in allowing saccadic movements. A black field with a single white spot which appears for 0.25 seconds at one end of the tablet held lengthwise from the patient (held in front approximately 16 inches away from patient). The Patient has on R/B goggles. Then the spot appears at the far end of the tablet one second later for 0.25 seconds. The spot continues to move away and toward athlete until it flashes with a color then stops. The athlete is then to touch as close as possible to the spot where the colored dot flashed. The software measures the difference in mm between the actual location of the dot and the spot where the patient touches his/her finger. The test is repeated with two red, two blue and two gray dots. Two of the dots were only seen by right eye. Two were seen by left and two by both eyes. This tests the saccadic system on right eye, left eye and binocularly.

In at least one embodiment, the method further includes conducting a real-time saccades test 212 for mild traumatic brain injury or concussion utilizing the user interface, the user input device, and the associated portable hand-held computer 316. The method includes displaying repeatedly a white dot on a black screen on the user interface for interaction and response from the test subject, and wherein each white dot further comprises an alphabetical letter within the dot. The method includes detecting user interaction and response by the test subject on the user interface 316, wherein the test subject is attempting to provide an input based on a cognitive decision about the letter 206 displayed in the white dot and its relation to a predetermined test criteria provided to the test subject 210. The arrow keys or the like on a tablet can be linked to the alphabet order 208. The method includes recording a plurality of data points 110 to measure and record the input data from the test subject. The method includes analyzing with the computer 316 the user interaction, response, and input of the test subject 310. The method includes determining with the computer whether the input test subject exhibits a reduction in cerebral function presumably resulting from a mild traumatic brain injury, such as a concussion.

Also by way of example, and not of limitation, in this alternate Saccades test; however, instead of just seeing a white dot on a black screen, one would see a small letter on each white dot. Instead of touching where the white dot is, one would have to make a decision. For example, touch the left arrow if the letter is a lower case letter that occurs alphabetically before the letter 'm'. If the letter appears after the letter 'm', tough the right arrow. If the letter is capitalized, though the up arrow. Up to 20 letters are displayed with six upper-cased, seven before, and seven after "m". This will better test saccades as the letter will appear for 0.5 sec. This will also test some cognitive skills.

In at least one embodiment, the method also includes conducting a real-time pursuits test 214 for mild traumatic brain injury or concussion utilizing the user interface, the user input device, and the associated portable hand-held computer. The method includes displaying a moving icon on the user interface 316 for interaction and response from the test subject 310. The method includes detecting user interaction and response by the test subject on the user interface, wherein the test subject is attempting to touch and follow by fingertip the moving icon for a predetermined number of attempts. The method includes recording a plurality of data points to measure the accuracy of the test subject in following the moving icon. The method includes analyzing with the computer the user interaction, response, and input of the test subject. The method includes determining with the computer whether the input test subject exhibits a reduction in cerebral function presumably resulting from a mild traumatic brain injury, such as a concussion.

Also by way of example, and not of limitation, in this pursuits test, one will try to keep his or hand on a moving spot. It will move in different directions and at different speeds. The system will keep track of the distance that the finger is from the center of the spot.

Also by way of example, and not of limitation, in this pursuits test, different parts of the brain are used to cause pursuit movements. The tablet is still held in same position. Now an athlete/test subject is instructed to follow black field with white dot which moves in an elliptical path around the tablet. Movement occurs at a speed to be set after testing which is about 80% of maximum normal can follow. As the spot is moving it flashes every second for 0.2 seconds to 50% brighter. One of these flashes the light changes to red and disappears after 0.2 seconds. The athlete is instructed to touch where the light was when it last flashed. The test is done six times with twice red, twice blue, and twice gray. This tests pursuits which are monocular right side and left side as well as binocularly.

In at least one embodiment, the an alternative pursuits method also includes: conducting a real-time pursuits test 214 for mild traumatic brain injury or concussion utilizing the user interface, the user input device, and the associated portable hand-held computer; displaying a moving icon on the user interface 316 for interaction and response from the test subject 310, wherein the moving icon further is displaying within the icon a changing number or letter that changes at a predetermined time interval; detecting user interaction and response by the test subject 310 on the user interface 316, wherein the test subject is attempting to follow the moving icon with his or her eyes and responding on the user interface based upon a direction in which the changing number or letter changes or where it falls in sequence, for a predetermined number of attempts; recording a plurality of data points to measure the accuracy of the test subject in following the moving icon; analyzing with the computer the user interaction, response, and input of the test subject; and determining with the computer whether the input test subject exhibits a reduction in cerebral function presumably resulting from a mild traumatic brain injury, such as a concussion.

By way of example, and not of limitation, in this alternate real-time pursuits test 214 can include within the moving icon, such as a white dot, a letter (a, b, c, . . . ) or number (1, 2, 3, . . . ) that changes with a flash at a predetermined time interval, such as to flash for 0.25 seconds. As the test subject 310 follows the white dot in the screen, he or she observes and looks for lower case letters and, for example, whether the letter falls before or after the letter "m." For example, in a test, one third of the letters can be before "m" and one third after "m" while the remaining one third are capitalized. Keys or input devices on the user interface can be utilized. For example it at least one embodiment the arrow keys are used to provide a response. The number of errors are recorded, and thus track how well the test subject was pursing the moving dot. Additionally, the moving icon can include numbers. The numbers can change and the test subject would respond accordingly based on the test instructions, such as where the number falls relative to same base number.

In at least one embodiment, the method also includes conducting a real-time combined fixation, vestibular, and proprioception test 216 for mild traumatic brain injury or concussion utilizing the user interface, the user input device, and the associated portable hand-held computer. The method includes displaying a moving icon on the user interface that visually represents a ball bearing that can roll around freely on the screen for interaction and response from the test subject. The method includes displaying a circular shape on the user interface, wherein the object of the test subject is to keep the moving icon within the circular shape and not roll out. The method includes detecting user interaction and response by the test subject 310 on the user interface 316, wherein the test subject 310 is attempting to keep the moving icon within the circular shape and not roll out for a predetermined number of attempts, 112, 114. The method includes recording a plurality of data points to measure the accuracy of the test subject in following the moving icon. The method includes analyzing with the computer the user interaction, response, and input of the test subject. The method includes determining with the computer 316 whether the input test subject 310 exhibits a reduction in cerebral function presumably resulting from a mild traumatic brain injury, such as a concussion.

By way of example, and not of limitation, in this third test (proprioception and fixation), imagine a ball bearing on a plate of glass. Have the athlete/test subject stand and hold the tablet with the virtual ball bearing and have them keep it inside a drawn circle of one inch diameter during a one minute test. The software tests the amount of time the ball bearing is outside a range that has been determined in testing control subjects such that 95% of the time the controls are able to keep the bearing within this area. This is testing their visual system including their vestibular, hand-eye, fixation (if the bubble is very small) system as well as their proprioception system.

Also by way of example, and not of limitation, in this third test (proprioception and fixation), the ball changes its direction and speed every 5 seconds. One must react to this change without and clue as to what the change is. There is the same number and same speed changes for the first fifteen seconds as the last fifteen seconds. The directions are complementary and equal.

In at least one embodiment, test scenario, the test subject is rotated again after the first and second tests and before the third test commences. This test will test fixation, pursuits, vestibular and proprioception. The distance from the center of the screen is tracked.

In at least one embodiment, the method further includes: conducting a real-time photo differentiation recognition test for mild traumatic brain injury or concussion utilizing the user interface, the user input device, and the associated portable hand-held computer. The method includes displaying a photo on the user interface 316 depicting a typical object or person but having at least one atypical attribute to the object or person. The method includes displaying subsequently, and in varying degrees of rotation, a plurality of photos with only one of the plurality matching the one with at least one atypical attribute, such that the test subject 310 must select a photo pair that matches. The method includes detecting user interaction and response by the test subject 310 on the user interface 316, wherein the test subject 310 is attempting to match a pair of photos having at least one atypical attribute to the object or person. The method includes recording a plurality of data points to measure the accuracy of the test subject in matching a pair of photos having at least one atypical attribute to the object or person.

The method includes analyzing with the computer the user interaction, response, and input of the test subject. The method includes determining with the computer whether the input test subject exhibits a reduction in cerebral function presumably resulting from a mild traumatic brain injury, such as a concussion.

In at least one embodiment, the method also includes selecting and conducting two or more the following tests on the test subject 310 in order: conducting a real-time saccades test for mild traumatic brain injury or concussion utilizing the user interface, the user input device, and the associated portable hand-held computer; conducting a real-time pursuits test for mild traumatic brain injury or concussion utilizing the user interface, the user input device, and the associated portable hand-held computer; conducting a real-time combined fixation, vestibular, and proprioception test for mild traumatic brain injury or concussion utilizing the user interface, the user input device, and the associated portable hand-held computer; and conducting a real-time photo differentiation recognition test for mild traumatic brain injury or concussion utilizing the user interface, the user input device, and the associated portable hand-held computer.

In at least one embodiment, the method further includes rotating 104, 108, before and/or between any one or more the real-time saccades test, real-time pursuits test, the real-time combined fixation, vestibular, and proprioception test, and the real-time photo differentiation recognition test, the test subject holding the portable hand-held computer 316 a predetermined number of revolutions, and at a predetermined rate of rotation, to engage the vestibular system of the test subject prior to testing for mild traumatic brain injury or concussion.

In at least one embodiment, the method also includes using a computer program on the computer to time the speed of turning a the test subject prior to conducting a test 106 when rotating the test subject holding the portable hand-held computer a predetermined number of revolutions, and at a predetermined rate of rotation, to engage the vestibular system of the test subject prior to testing for mild traumatic brain injury or concussion.

In at least one embodiment, the method further includes using a rotating image 108 held by the test subject while rotating in order to adjust the speed of rotation.

In at least one embodiment, the method also includes using a cumulative sum of a plurality of distances 110 measured each portion of a second from a moving circle on the computer user interface to determine how well the test subject maintains visual contact with a target.

In at least one embodiment, the method also includes wherein the computer device utilized further comprises a plurality of accelerometers 112 in the computer device to determine reaction abilities of the test subject.

In at least one embodiment, the method further includes wherein the computer device utilized further comprises a plurality of accelerometers 114 in the computer device to monitor changes over time in a reaction ability of the test subject.

In at least one embodiment, the method also includes recording a reaction 202 of the test subject 310 to a force being applied without their being aware of the timing or the amount of force.

In at least one embodiment, the method further includes using unknown forces 204 to determine reaction time changes over time in the test subject 310.

In at least one embodiment, the method also includes using alphabetical order of letters 206 in the test conducted to determine cognitive damage caused by concussion or mild traumatic brain injury.

In another exemplary embodiment, the technology described herein provides a computer program product for testing a subject to detect a reduction in cerebral function presumably resulting from a mild traumatic brain injury, such as a concussion, that affects one or more of visual, proprioceptive, and vestibular brain functions. The computer program product includes: a computer readable storage medium readable by a processor of a computer and configured to store instructions for execution by the processor for performing a method including: providing a user interface, a user input device, and an associated portable hand-held computer into the hands of the test subject suspected of having a mild traumatic brain injury, such as a concussion; providing an icon on the screen of the user interface visible to the test subject; rotating the test subject holding the portable hand-held computer a predetermined number of revolutions, and at a predetermined rate of rotation, to engage the vestibular system of the test subject prior to testing for mild traumatic brain injury or concussion; aligning, by the test subject, the icon on the screen of the user interface in alignment with a test administrator; maintaining the alignment of the icon on the screen of the user interface and the test administrator throughout the rotations; conducting a real-time test for mild traumatic brain injury or concussion utilizing the user interface, the user input device, and the associated portable hand-held computer; displaying at least one test icon on the user interface for interaction and response from the test subject; detecting user interaction and response by the test subject on the user interface; analyzing with the computer the user interaction, response, and input of the test subject; and determining with the computer whether the input test subject exhibits a reduction in cerebral function presumably resulting from a mild traumatic brain injury, such as a concussion.

In another exemplary embodiment, the technology described herein provides an apparatus for testing a subject to detect a reduction in cerebral function presumably resulting from a mild traumatic brain injury, such as a concussion, that affects one or more of visual, proprioceptive, and vestibular brain functions. The apparatus including: a user interface; a user input device; and an associated portable hand-held computer configured for placement into the hands of the test subject suspected of having a mild traumatic brain injury, such as a concussion; the computer being programmed to: provide an icon on the screen of the user interface visible to the test subject; rotate the test subject holding the portable hand-held computer a predetermined number of revolutions, and at a predetermined rate of rotation, to engage the vestibular system of the test subject prior to testing for mild traumatic brain injury or concussion; align, by the test subject, the icon on the screen of the user interface in alignment with a test administrator; maintain the alignment of the icon on the screen of the user interface and the test administrator throughout the rotations; conduct a real-time test for mild traumatic brain injury or concussion utilizing the user interface, the user input device, and the associated portable hand-held computer; display at least one test icon on the user interface for interaction and response from the test subject; detect user interaction and response by the test subject on the user interface; analyze with the computer the user interaction, response, and input of the test subject; and determine with the computer whether the input test subject exhibits a reduction in cerebral function presumably resulting from a mild traumatic brain injury, such as a concussion.

Referring now to FIG. 1, a flowchart diagram 100 depicting a method and various method steps for testing a subject to detect a reduction in cerebral function presumably resulting from a mild traumatic brain injury, such as a concussion, that affects one or more of visual, proprioceptive, and vestibular brain functions.

Referring now to FIG. 2, a flowchart diagram 100 depicting additional, various method steps for testing a subject to detect a reduction in cerebral function presumably resulting from a mild traumatic brain injury, such as a concussion, that affects one or more of visual, proprioceptive, and vestibular brain functions.

The method steps depicted in FIGS. 1 and 2 do not necessarily occur sequentially and may vary as determined by a test administrator. Additionally, not all methods steps listed are required, as may be determined by a test administer. The steps listed are exemplary and may be varied in both order and selection.

Referring now to FIG. 3, a schematic diagram 300 is shown depicting a system testing a subject to detect a reduction in cerebral function presumably resulting from a mild traumatic brain injury, such as a concussion, that affects one or more of visual, proprioceptive, and vestibular brain functions.

The test subject/patient 310 may utilize a computer device such as a computer 314, smart device 312, or tablet 316 to access the assessment program. In an athletic event, such as a football game, a test administrator having a tablet can operate the program and administer tests at the sidelines. The computer device 212, 314, 316 can access the public network 320 wirelessly or tethered. The computer device 212, 314, 316 can access one or more remote servers 330 for the processing and or storing of data and utilize one or more databases 332 in network based implementations.

Figure 4:
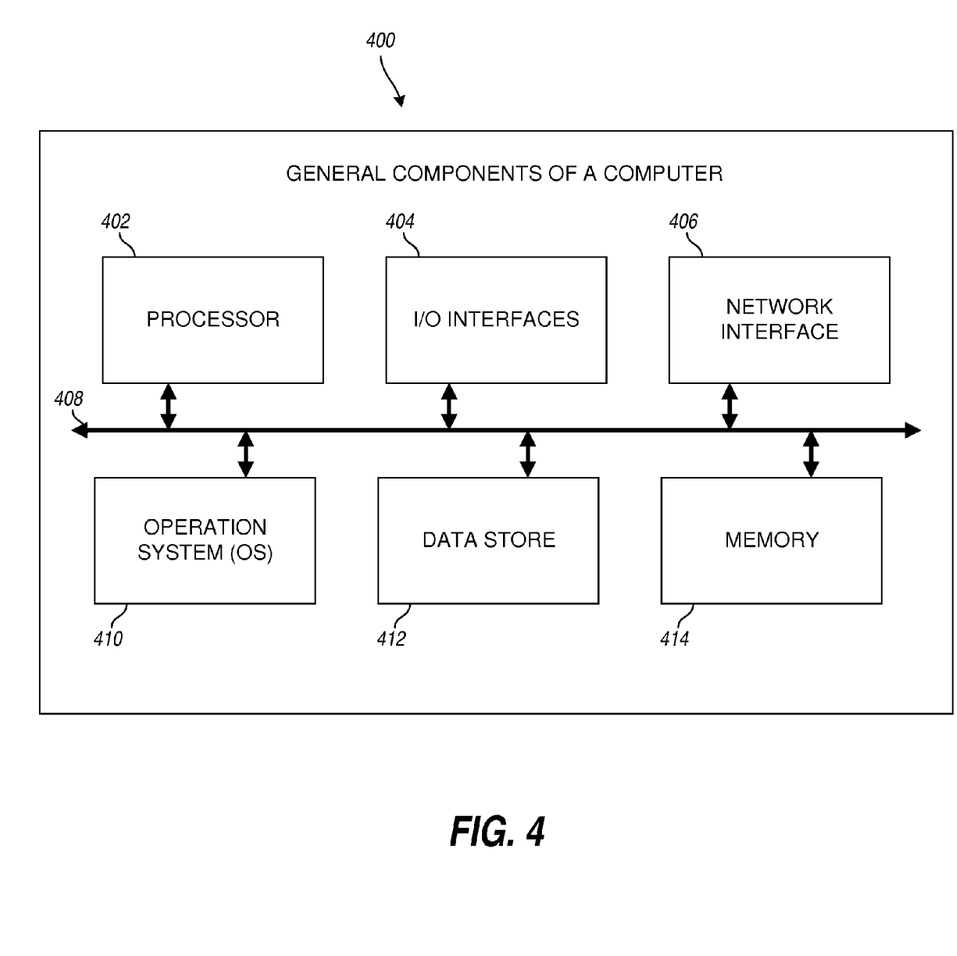
FIG. 4 is a block diagram illustrating the general components of a computer according to an exemplary embodiment of the technology.

Referring now to FIG. 4, a block diagram 400 illustrating the general components of a computer is shown. Any one or more of the computers, servers, database, and the like, disclosed above, may be implemented with such hardware and software components. The computer 400 can be a digital computer that, in terms of hardware architecture, generally includes a processor 402, input/output (I/O) interfaces 404, network interfaces 406, an operating system (O/S) 410, a data store 412, and a memory 414. The components (402, 404, 406, 410, 412, and 414) are communicatively coupled via a local interface 408. The local interface 408 can be, for example but not limited to, one or more buses or other wired or wireless connections, as is known in the art. The local interface 408 can have additional elements, which are omitted for simplicity, such as controllers, buffers (caches), drivers, among many others, to enable communications. Further, the local interface 408 can include address, control, and/or data connections to enable appropriate communications among the aforementioned components. The general operation of a computer comprising these elements is well known in the art.

The processor 402 is a hardware device for executing software instructions. The processor 402 can be any custom made or commercially available processor, a central processing unit (CPU), an auxiliary processor among several processors associated with the computer 400, a semiconductor-based microprocessor (in the form of a microchip or chip set), or generally any device for executing software instructions. When the computer 400 is in operation, the processor 402 is configured to execute software stored within the memory 414, to communicate data to and from the memory 414, and to generally control operations of the computer 400 pursuant to the software instructions.

The I/O interfaces 404 can be used to receive user input from and/or for providing system output to one or more devices or components. User input can be provided via, for example, a keyboard and/or a mouse. System output can be provided via a display device and a printer (not shown). I/O interfaces 404 can include, for example but not limited to, a serial port, a parallel port, a small computer system interface (SCSI), an infrared (IR) interface, a radio frequency (RF) interface, and/or a universal serial bus (USB) interface.

The network interfaces 406 can be used to enable the computer 400 to communicate on a network. For example, the computer 400 can utilize the network interfaces 408 to communicate via the internet to other computers or servers for software updates, technical support, etc. The network interfaces 408 can include, for example, an Ethernet card (e.g., 10BaseT, Fast Ethernet, Gigabit Ethernet) or a wireless local area network (WLAN) card (e.g., 802.11a/b/g). The network interfaces 408 can include address, control, and/or data connections to enable appropriate communications on the network.

A data store 412 can be used to store data, such as information regarding positions entered in a requisition. The data store 412 can include any of volatile memory elements (e.g., random access memory (RAM, such as DRAM, SRAM, SDRAM, and the like)), nonvolatile memory elements (e.g., ROM, hard drive, tape, CDROM, and the like), and combinations thereof. Moreover, the data store 412 can incorporate electronic, magnetic, optical, and/or other types of storage media. In one example, the data store 412 can be located internal to the computer 400 such as, for example, an internal hard drive connected to the local interface 408 in the computer 400. Additionally in another embodiment, the data store can be located external to the computer 400 such as, for example, an external hard drive connected to the I/O interfaces 404 (e.g., SCSI or USB connection). Finally in a third embodiment, the data store may be connected to the computer 400 through a network, such as, for example, a network attached file server.

The memory 414 can include any of volatile memory elements (e.g., random access memory (RAM, such as DRAM, SRAM, SDRAM, etc.)), nonvolatile memory elements (e.g., ROM, hard drive, tape, CDROM, etc.), and combinations thereof. Moreover, the memory 414 may incorporate electronic, magnetic, optical, and/or other types of storage media. Note that the memory 414 can have a distributed architecture, where various components are situated remotely from one another, but can be accessed by the processor 402.

The software in memory 414 can include one or more software programs, each of which includes an ordered listing of executable instructions for implementing logical functions. In the example of FIG. 4, the software in the memory system 414 includes the interactive toolkit for sourcing valuation and a suitable operating system (O/S) 410. The operating system 410 essentially controls the execution of other computer programs, such as the interactive toolkit for sourcing valuation, and provides scheduling, input-output control, file and data management, memory management, and communication control and related services. The operating system 410 can be any of Windows NT, Windows 2000, Windows XP, Windows Vista, Windows 7, 8, 10 (all available from Microsoft, Corp. of Redmond, Wash.), Solaris (available from Sun Microsystems, Inc. of Palo Alto, Calif.), LINUX (or another UNIX variant) (available from Red Hat of Raleigh, N.C.), or other like operating system with similar functionality.

In an exemplary embodiment of the technology described herein, the computer 400 is configured to perform flowcharts 100 and 200 depicted in FIGS. 1 and 2 respectively.

Although this technology has been illustrated and described herein with reference to preferred embodiments and specific examples thereof, it will be readily apparent to those of ordinary skill in the art that other embodiments and examples can perform similar functions and/or achieve like results. All such equivalent embodiments and examples are within the spirit and scope of the invention and are intended to be covered by the following claims.

What is claimed is:

1. A method for testing a subject to detect a reduction in cerebral function resulting from a mild traumatic brain injury or a concussion, that affects one or more of visual, proprioceptive, and vestibular brain functions, the method comprising:
    providing a user interface, a user input device, and an associated portable hand-held computer, having a processor and a memory and a non-transitory computer program product running in the portable hand-held computer, into the hands of the test subject suspected of having a mild traumatic brain injury;
    providing an icon on the screen of the user interface visible to the test subject;
    rotating the test subject holding the portable hand-held computer a predetermined number of revolutions, and at a predetermined rate of rotation, to engage the vestibular system of the test subject prior to testing for mild traumatic brain injury or concussion;
    aligning, by the test subject, the icon on the screen of the user interface in alignment with a test administrator; and
    maintaining the alignment of the icon on the screen of the user interface and the test administrator throughout the rotations.

2. The method of claim 1, further comprising:
    conducting a real-time test for mild traumatic brain injury or concussion utilizing the user interface, the user input device, and the associated portable hand-held computer;
    displaying at least one test icon on the user interface for interaction and response from the test subject;
    detecting by the computer program and processor user interaction and response by the test subject on the user interface of the hand-held computer;
    measuring, by the computer program and processor, a plurality of interactions and responses from the test subject in response to the test icon;
    analyzing, as calculated by the computer program and processor using a cumulative sum of a plurality of distances measured each portion of a second from the test icon on the computer user interface, the user interaction, response, and input of the test subject to determine how well the test subject maintains visual contact with the test icon; and
    determining with the computer program and processor whether the input test subject exhibits a reduction in cerebral function resulting from a mild traumatic brain injury based upon how well the test subject maintains visual contact with the test icon and interacts with and responds to the test icon.

3. The method of claim 2, further comprising:
comparing, by the computer program and processor, a real-time performance and results of the test subject with a previously established baseline performance.

4. The method of claim 2, further comprising:
recording a reaction of the test subject to a force being applied without their being aware of the timing or the amount of force.

5. The method of claim 2, further comprising:
using a plurality of forces to determine reaction time changes over time in the test subject, wherein the plurality of forces are known to a tester yet are unknown to the test subject in order to challenge the test subject.

6. The method of claim 2, further comprising:
using alphabetical order of letters in the test conducted to determine cognitive damage caused by concussion or mild traumatic brain injury.

7. The method of claim 1, further comprising:
conducting a real-time saccades test for mild traumatic brain injury or concussion utilizing the user interface, the user input device, and the associated portable hand-held computer;
displaying repeatedly a white dot on a black screen on the user interface for interaction and response from the test subject;
detecting by the computer program and processor user interaction and response by the test subject on the user interface of the hand-held computer, wherein the test subject is attempting to touch the white dot for a predetermined number of attempts;
measuring, by the computer program and processor, a plurality of interactions and responses from the test subject in response to the white dot;
recording, by the computer program and processor, a plurality of data points to measure a distance between the white dot and a location on the user interface touched by the test subject trying to touch the white dot;
analyzing, as calculated by the computer program and processor using a cumulative sum of a plurality of distances measured each portion of a second from the white dot on the computer user interface the user interaction, response, and input of the test subject to determine how well the test subject maintains visual contact with the white dot; and
determining with the computer program and processor whether the input test subject exhibits a reduction in cerebral function resulting from a mild traumatic brain injury based upon how well the test subject maintains visual contact with the white dot and interacts with and responds to the white dot.

8. The method of claim 1, further comprising:
conducting a real-time saccades test for mild traumatic brain injury or concussion utilizing the user interface, the user input device, and the associated portable hand-held computer;
displaying repeatedly a white dot on a black screen on the user interface for interaction and response from the test subject, and wherein each white dot further comprises an alphabetical letter within the dot;
detecting by the computer program and processor user interaction and response by the test subject on the user interface of the hand-held computer, wherein the test subject is attempting to provide an input based on a cognitive decision about the letter displayed in the white dot and its relation to a predetermined test criteria provided to the test subject;
measuring, by the computer program and processor, a plurality of interactions and responses from the test subject in response to the white dot and alphabetical letter;
recording, by the computer program and processor, a plurality of data points to measure and record the input data from the test subject to measure a distance between the white dot and a location on the user interface touched by the test subject trying to touch the white dot and alphabetical letter;
analyzing, as calculated by the computer program and processor using a cumulative sum of a plurality of distances measured each portion of a second from the white dot on the computer user interface the user interaction, response, and input of the test subject to determine how well the test subject maintains visual contact with the white dot and alphabetical letter; and
determining with the computer program and processor whether the input test subject exhibits a reduction in cerebral function resulting from a mild traumatic brain injury based upon how well the test subject maintains visual contact with the white dot and interacts with and responds to the white dot.

9. The method of claim 1, further comprising:
conducting a real-time pursuits test for mild traumatic brain injury or concussion utilizing the user interface, the user input device, and the associated portable hand-held computer;
displaying a moving icon on the user interface for interaction and response from the test subject;
detecting by the computer program and processor user interaction and response by the test subject on the user interface of the hand-held computer, wherein the test subject is attempting to touch and follow by fingertip the moving icon for a predetermined number of attempts;
measuring, by the computer program and processor, a plurality of interactions and responses from the test subject in response to the moving icon;
recording, by the computer program and processor, a plurality of data points to measure the accuracy of the test subject in following the moving icon;
analyzing as calculated by the computer program and processor using a cumulative sum of a plurality of distances measured each portion of a second the user interaction, response, and input of the test subject to determine how well the test subject maintains visual contact with the moving icon; and
determining with the computer program and processor whether the input test subject exhibits a reduction in cerebral function resulting from a mild traumatic brain injury based upon how well the test subject maintains visual contact with the moving icon and interacts with and responds to the moving icon;
detecting with the computer program and processor user interaction and response by the test subject on the user interface, wherein the test subject is attempting to provide an input based on a cognitive decision about the letter displayed in the white dot and its relation to a predetermined test criteria provided to the test subject.

10. The method of claim 1, further comprising:
conducting a real-time pursuits test for mild traumatic brain injury or concussion utilizing the user interface, the user input device, and the associated portable hand-held computer;

displaying a moving icon on the user interface for interaction and response from the test subject, wherein the moving icon further is displaying within the icon a changing number or letter that changes at a predetermined time interval;
detecting by the computer program and processor user interaction and response by the test subject on the user interface of the hand-held computer, wherein the test subject is attempting to follow the moving icon with his or her eyes and responding on the user interface based upon a direction in which the changing number or letter changes or where it falls in sequence, for a predetermined number of attempts;
measuring, by the computer program and processor, a plurality of interactions and responses from the test subject in response to the moving icon;
recording, by the computer program and processor, a plurality of data points to measure the accuracy of the test subject in following the moving icon;
analyzing, as calculated by the computer program and processor, the user interaction, response, and input of the test subject to determine how well the test subject maintains visual contact with the moving icon; and
determining with the computer program and processor whether the input test subject exhibits a reduction in cerebral function resulting from a mild traumatic brain injury based upon how well the test subject maintains visual contact with the moving icon and interacts with and responds to the moving icon.

11. The method of claim 1, further comprising:
conducting a real-time combined fixation, vestibular, and proprioception test for mild traumatic brain injury or concussion utilizing the user interface, the user input device, and the associated portable hand-held computer;
displaying a moving icon on the user interface that visually represents a ball bearing that can roll around freely on the screen for interaction and response from the test subject;
displaying a circular shape on the user interface, wherein the object of the test subject is to keep the moving icon within the circular shape and not roll out;
detecting by the computer program and processor user interaction and response by the test subject on the user interface of the hand-held computer, wherein the test subject is attempting to keep the moving icon within the circular shape and not roll out for a predetermined number of attempts;
measuring, by the computer program and processor, a plurality of interactions and responses from the test subject in response to the moving icon and the circular shape;
recording, by the computer program and processor, a plurality of data points to measure the accuracy of the test subject in following the moving icon in relation to the circular shape;
analyzing as calculated by the computer program and processor the user interaction, response, and input of the test subject to determine how well the test subject maintains visual contact with the moving icon and circular shape; and
determining with the computer program and processor whether the input test subject exhibits a reduction in cerebral function resulting from a mild traumatic brain injury based upon how well the test subject maintains visual contact with the test icon and interacts with and responds to the moving icon.

12. The method of claim 1, further comprising:
conducting a real-time photo differentiation recognition test for mild traumatic brain injury or concussion utilizing the user interface, the user input device, and the associated portable hand-held computer;
displaying a photo on the user interface depicting a typical object or person but having at least one atypical attribute to the object or person;
displaying subsequently, and in varying degrees of rotation, a plurality of photos with only one of the plurality matching the one with at least one atypical attribute, such that the test subject must select a photo pair that matches;
detecting by the computer program and processor user interaction and response by the test subject on the user interface of the hand-held computer, wherein the test subject is attempting to match a pair of photos having at least one atypical attribute to the object or person;
measuring, by the computer program and processor, a plurality of interactions and responses from the test subject in response to the plurality of photos;
recording, by the computer program and processor, a plurality of data points to measure the accuracy of the test subject in matching a pair of photos having at least one atypical attribute to the object or person;
analyzing as calculated by the computer program and processor the user interaction, response, and input of the test subject to determine how well the test subject matches photo pairs; and
determining with the computer program and processor whether the input test subject exhibits a reduction in cerebral function resulting from a mild traumatic brain injury based upon how well the test subject matches photo pairs.

13. The method of claim 1, further comprising:
selecting and conducting two or more the following tests on the test subject in order:
conducting a real-time saccades test for mild traumatic brain injury or concussion utilizing the user interface, the user input device, and the associated portable hand-held computer;
conducting a real-time pursuits test for mild traumatic brain injury or concussion utilizing the user interface, the user input device, and the associated portable hand-held computer;
conducting a real-time combined fixation, vestibular, and proprioception test for mild traumatic brain injury or concussion utilizing the user interface, the user input device, and the associated portable hand-held computer; and
conducting a real-time photo differentiation recognition test for mild traumatic brain injury or concussion utilizing the user interface, the user input device, and the associated portable hand-held computer.

14. The method of claim 13, further comprising:
rotating, before and/or between any one or more the real-time saccades test, real-time pursuits test, the real-time combined fixation, vestibular, and proprioception test, and the real-time photo differentiation recognition test, the test subject holding the portable hand-held computer a predetermined number of revolutions, and at a predetermined rate of rotation, to engage the vestibular system of the test subject prior to testing for mild traumatic brain injury or concussion.

15. The method of claim 1, further comprising:
using a computer program on the computer to time the speed of turning a the test subject prior to conducting a test when rotating the test subject holding the portable hand-held computer a predetermined number of revolutions, and at a predetermined rate of rotation, to engage the vestibular system of the test subject prior to testing for mild traumatic brain injury or concussion.

16. The method of claim 1, further comprising:
using a rotating image held by the test subject while rotating in order to adjust a speed of rotation.

17. The method of claim 1, further comprising:
using a cumulative sum of a plurality of distances measured each portion of a second from a moving circle on the computer user interface to determine how well the test subject maintains visual contact with a target.

18. The method of claim 1, wherein the computer device utilized further comprises:
a plurality of accelerometers in the computer device to determine reaction abilities of the test subject.

19. The method of claim 1, wherein the computer device utilized further comprises:
a plurality of accelerometers in the computer device to monitor changes over time in a reaction ability of the test subject.

20. A non-transitory computer program product for testing a subject by an examiner to detect a reduction in cerebral function resulting from a mild traumatic brain injury, or concussion, that affects one or more of visual, proprioceptive, and vestibular brain functions, the non-transitory computer program product comprising:
a computer readable storage medium readable by a processor of a computer and configured to store instructions for execution by the processor for performing a method comprising:
providing a user interface, a user input device, and an associated portable hand-held computer into the hands of the test subject suspected of having a mild traumatic brain injury;
providing an icon on the screen of the user interface visible to the test subject for maintaining alignment, by the test subject, with the examiner throughout rotation of the test subject holding the portable hand-held computer a predetermined number of revolutions, and at a predetermined rate of rotation, to engage the vestibular system of the test subject prior to testing for mild traumatic brain injury or concussion;
conducting a real-time test for mild traumatic brain injury or concussion utilizing the user interface, the user input device, and the associated portable hand-held computer;
displaying at least one test icon on the user interface for interaction and response from the test subject;
detecting user interaction and response by the test subject on the user interface;
analyzing with the computer the user interaction, response, and input of the test subject; and
determining with the computer whether the input test subject exhibits a reduction in cerebral function resulting from a mild traumatic brain injury.

21. An apparatus for testing by an examiner a subject to detect a reduction in cerebral function resulting from a mild traumatic brain injury, or concussion, that affects one or more of visual, proprioceptive, and vestibular brain functions, the apparatus comprising:
a user interface;
a user input device; and
an associated portable hand-held computer configured for placement into the hands of the test subject suspected of having a mild traumatic brain injury;
the computer being programmed to:
provide an icon on the screen of the user interface visible to the test subject for maintaining alignment, by the test subject, with the examiner throughout rotation of the test subject holding the portable hand-held computer a predetermined number of revolutions, and at a predetermined rate of rotation, to engage the vestibular system of the test subject prior to testing for mild traumatic brain injury or concussion;
conduct a real-time test for mild traumatic brain injury or concussion utilizing the user interface, the user input device, and the associated portable hand-held computer;
display at least one test icon on the user interface for interaction and response from the test subject;
detect user interaction and response by the test subject on the user interface;
analyze with the computer the user interaction, response, and input of the test subject; and
determine with the computer whether the input test subject exhibits a reduction in cerebral function resulting from a mild traumatic brain injury.

* * * * *